United States Patent [19]

Sauers

[11] 4,160,034
[45] Jul. 3, 1979

[54] SUBSTITUTED CARBAMATES

[75] Inventor: Richard F. Sauers, Hockessin, Del.

[73] Assignee: E. I. Du Pont de Nemours and Company, Wilmington, Del.

[21] Appl. No.: 885,251

[22] Filed: Mar. 10, 1978

Related U.S. Application Data

[63] Continuation-in-part of Ser. No. 812,316, Jul. 1, 1977, abandoned.

[51] Int. Cl.$^2$ .................. A01N 9/12; C07C 119/18
[52] U.S. Cl. ........................... 424/298; 260/453 RW
[58] Field of Search ................ 260/453 RW; 424/298

[56] References Cited

U.S. PATENT DOCUMENTS

| | | | |
|---|---|---|---|
| 3,344,153 | 9/1967 | Kuhle | 424/300 |
| 4,004,031 | 1/1977 | Drabek | 424/298 |

*Primary Examiner*—Natalie Trousof
*Assistant Examiner*—Robert C. Whittenbaugh

[57] ABSTRACT

Insecticidal carbamates, such as dimethyl N,N'-[[1,2-ethanediylbis[thio(methylimino)carbonyloxy]]]bis(ethaneimidothioate) for control of pestiferous insects belonging to such orders as Lepidoptera, Coleoptera and Diptera.

12 Claims, No Drawings

SUBSTITUTED CARBAMATES

CROSS-REFERENCE TO RELATED APPLICATIONS

This is a continuation-in-part application of U.S. Ser. No. 812,316 filed July 1, 1977 and now abandoned.

BACKGROUND OF THE INVENTION

This invention relates to insecticidal carbamates.

Belgian Pat. No. 848,912, granted May 21, 1977, relates to insecticidal symmetrical bis-carbamoyl sulfide compounds of the following general formula:

$$RO-\overset{O}{\underset{\|}{C}}-\overset{R'}{\underset{|}{N}}-S-\overset{R'}{\underset{|}{N}}-\overset{O}{\underset{\|}{C}}-OR$$

wherein:

R is:

$$\underset{R_3}{\overset{R_2}{\diagdown}}C=N-\quad\text{or}\quad \left(\underset{A}{\bigcirc}\right)C=N-\quad\text{and}$$

R' is alkyl containing from one to four carbon atoms.

Among the numerous compounds which are included in the Belgian patent are those wherein $R_2$ is alkyl, optionally substituted with one or more alkylthio groups, and wherein $R_3$ is hydrogen alkyl or alkoxy. The patentee states, however, that while compounds according to the above formula wherein $R_2$ is an alkylthioalkyl substituent and $R_3$ is hydrogen exhibit good pesticidal activity, their mammalian toxicity is unacceptably high.

U.S. Pat. No. 4,004,031 issued Jan. 18, 1977, discloses insecticidal compounds of the formula:

$$CH_3-\underset{R-S}{\overset{}{C}}=NO-\overset{O}{\underset{\|}{C}}-\overset{}{\underset{CH_3}{N}}-S-\overset{}{\underset{CH_3}{N}}-\overset{O}{\underset{\|}{C}}-O-N=\overset{}{\underset{S-R}{C}}-CH_3$$

wherein R is an alkyl group of one to five carbons.

U.S. Pat. No. 3,576,834 issued Apr. 27, 1971, relates to insecticidal compounds having the structure:

$$R_1-\underset{R_4-Q}{\overset{}{C}}=NO-\overset{O}{\underset{\|}{C}}-N\underset{R_3}{\overset{R_2}{\diagup}},$$

such as methomyl.

SUMMARY OF THE INVENTION

This invention relates to compounds of Formula I, to insecticidal compositions containing them and to the method of using said compounds as insecticides:

$$R-\underset{R_1S}{\overset{}{C}}=NO\overset{O}{\underset{\|}{C}}N-S-R_2-S-N\overset{O}{\underset{\|}{C}}ON=\underset{SR_1}{\overset{}{C}}-R \quad (I)$$

wherein

R is a branched or straight chain alkyl group of 1–3 carbon atoms or $CH_2OCH_3$;

$R_1$ is a branched or straight chain alkyl group of 1–3 carbon atoms;

$R_2$ is $-CH_2CH_2-$, $$-CH_2\overset{CH_3}{\underset{|}{CH}}-$$

or $-CH_2CH_2ZCH_2CH_2-$; and

Z is oxygen or sulfur.

DETAILED DESCRIPTION OF THE INVENTION

Preferred Compounds

Compounds which are preferred for their high insecticidal activity are those compounds of Formula I wherein R is methyl or ethyl; and $R_1$ is methyl.

More preferred for their higher insecticidal activity are those compounds of Formula I wherein R is methyl;

$R_1$ is methyl; and $R_2$ is $-CH_2CH_2-$.

Specifically preferred for its outstanding insecticidal activity is dimethyl N,N'[[1,2-ethanediylbis[thio(methylimino)carbonyloxy]]]bis(ethaneimidothioate).

Preparation

The compounds of Formula I can be prepared, as shown in Equation A, by reacting at least two moles of a substituted N-(aminocarbonyloxy)-alkanimidothioic acid ester of Formula II with one mole of an alkane disulfenyl halide of Formula III in the presence of base:

Equation A $$2\ R-\underset{R_1S}{\overset{}{C}}=NO\overset{O}{\underset{\|}{C}}-\underset{CH_3}{\overset{}{N}}-H \quad + \quad XS-R_2-SX \longrightarrow$$

(II) \qquad (III)

$$R-\underset{R_1S}{\overset{}{C}}=NO\overset{O}{\underset{\|}{C}}N-S-R_2-S-N\overset{O}{\underset{\|}{C}}ON=\underset{SR_1}{\overset{}{C}}-R \quad (I)$$

wherein R, $R_1$, and $R_2$ are as previously defined and X is halogen.

The reaction can be carried out in any organic solvent which is inert to the reactants and the reaction products, e.g. methylene chloride, dioxane, tetrahydrofuran, chloroform, 1,2-dichlorethane, acetonitrile, benzene, toluene, the xylenes, acetone or methyl ethyl ketone. Mixtures of such solvents can also be used. A base which will function as an acid acceptor can be used in synthesizing the compounds of this invention.

The process can be carried out at a temperature of between about $-20°$ and $60°$ C., preferably between about $-5°$ and $40°$ C. Pressure is not critical; for convenience, atmospheric pressure is preferred.

Preparation of the compounds of Formula II used as starting materials is described in U.S. Pat. Nos. 3,574,736; 3,576,834 and 3,787,470.

In the compounds of Formula III, chlorine is the preferred halogen for economic reasons, and those compounds can be prepared by a suitable modification of the methods described in the *Journal of Heterocyclic Chemistry*, 6, 629 (1969). Alkane sulfenyl halides, such as those of Formula III wherein X is fluorine, bromine, or iodine, are also known and may be prepared by the methods reviewed in *Synthesis*, 11, 561–580 (1970).

In the examples which follow, temperatures are given in degrees centigrade.

EXAMPLE 1

Ethane-1,2-bisthioacetate

To a solution of 141 g of sodium methoxide in 1 l of absolute ethanol, under a dry nitrogen atmosphere, was added 200 g of thiolacetic acid dropwise with stirring over a period of 20 minutes. Ethylene dibromide (229.2 g) was then added and the reaction heated to reflux for five hours. The reaction mixture was cooled, sodium bromide was filtered off, and the ethanol was removed under vacuum. The residue was taken up in diethyl ether, washed with water, dried over anhydrous magnesium sulfate and the crude product isolated by distillation of the diethyl ether solvent. After recrystallization from hexanes, the product, ethane-1,2-bisthiolacetate, melted at 68°–70°.

EXAMPLE 2

Ethane-1,2-Disulfenyl Chloride

Sulfuryl chloride (54 g) was added dropwise to a solution of 35.6 g of ethane-1,2-bisthiolacetate in 200 ml of methylene chloride at ambient temperature. After stirring for 45 minutes at room temperature the methylene chloride solvent and volatile by-products were removed by vacuum distillation of 0°. The yellow product, ethane-1,2-disulfenyl chloride, melted at 32°–34°.

EXAMPLE 3

Dimethyl N,N'[[1,2-ethanediylbis[thio(methylimino)carbonyloxy]]]bis(ethanimidothioate)

A solution of 6.5 g of N-(methylaminocarbonyloxy)ethanimidothioic acid, methyl ester, in 50 ml methylene chloride and 2.0 ml of pyridine was prepared. To that solution was added dropwise 28 gm of ethane-1,2-disulfenyl chloride, dissolved in 25 ml of methylene chloride, with stirring over a period of 10 minutes. The reaction was slightly exothermic. After stirring for about 16 hours at ambient temperature, the reaction mixture was washed with water, dried over anhydrous magnesium sulfate, and the crude product isolated by distilling off the methylene chloride solvent. After recrystallization from ethyl alcohol followed by recrystallization from acetonitrile, the product, dimethyl N,N'-[[1,2-ethanediylbis[thio(methylimino)carbonyloxy]]]bis(ethanimidothioate), melted at 176°–179°.

By reacting equivalent amounts of other compounds of Formula II with compounds of Formula III using the procedures of Examples 1, 2, and 3, the following compounds of Formula I can be prepared.

Table I $$\begin{array}{c} SR_1 \quad O \qquad\qquad\qquad O \quad SR_1 \\ | \quad\; \| \qquad\qquad\qquad \| \quad\; | \\ R-C=NOC-N-S-R_2-S-N-C-ON=C-R \\ \qquad\qquad | \qquad\qquad\quad | \\ \qquad\qquad CH_3 \qquad\qquad CH_3 \end{array}$$

| R | $R_1$ | $R_2$ |
|---|---|---|
| $CH_3$ | $C_2H_5$ | $-CH_2CH_2-$ |
| $CH_3$ | $nC_3H_7$ | $-CH_2CH_2-$ |
| $CH_3$ | $i-C_3H_7$ | $-CH_2CH_2-$ |
| $CH_3OCH_2$ | $CH_3$ | $-CH_2CH_2-$ |
| $C_2H_5$ | $CH_3$ | $-CH_2CH_2-$ |
| $nC_3H_7$ | $CH_3$ | $-CH_2CH_2-$ |
| $i-C_3H_7$ | $CH_3$ | $-CH_2CH_2-$ |
| $C_2H_5$ | $C_2H_5$ | $-CH_2CH_2-$ |
| $C_2H_5$ | $i-C_3H_7$ | $-CH_2CH_2-$ |
| $C_2H_5$ | $n-C_3H_7$ | $-CH_2CH_2-$ |
| $n-C_3H_7$ | $C_2H_5$ | $-CH_2CH_2-$ |
| $i-C_3H_7$ | $C_2H_5$ | $-CH_2CH_2-$ |
| $CH_3$ | $CH_3$ | $-CH_2CH_2OCH_2CH_2-$ |
| $CH_3$ | $C_2H_5$ | $-CH_2CH_2OCH_2CH_2-$ |
| $C_2H_5$ | $CH_3$ | $-CH_2CH_2OCH_2CH_2-$ |
| $CH_3$ | $CH_3$ | $-CH_2CH_2SCH_2CH_2-$ |

Formulation

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength conpositions are primarily used as intermediates for further formulation. The formulations, broadly, contain about 1% to 99% by weight of active ingredient(s) and at least one of (a) about 0% to 20% surfactant(s) and (b) about 1% to 99% solid or liquid diluent(s). More specifically, they will contain these ingredients in the following approximate proportions:

| | Percent by Weight* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

*Active Ingredient plus at least one of a Surfactant or Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers," 2nd Edn., Dorland Books, Caldwell, N.J. The more absorptive diluents are preferred for wettable powders and the denser ones for dusts. Typical liquid diluents and solvents are described in Marsden, "Solvent Guide," 2nd Edn., Interscience, New York, 1950. Solubility under 0.1% is preferred for suspension concentrates; solution concentrates are preferably stable against phase separation at 0° C. "McCutcheon's Detergents and Emulsifiers Annual," McCutcheon Division, MC Publishing Co., Ridgewood, N.J., as well as Sisely and Wood, "Encyclopedia of Surface Active Agents," Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques.

See J. E. Browning, "Agglomeration," *Chemical Engineering*, Dec. 4, 1967, pp. 147ff. and "Perry's Chemical Engineer's Handbook," 4th Edn., McGraw-Hill, N.Y., 1963, pp. 8–59ff.

For further information regarding the art of formulation, see for example:

J. B. Buchanan, U.S. Pat. No. 3,576,834 Apr. 27, 1971, Col. 5, line 36 through Col. 7, line 70 and Exs. 1–4, 17, 106, 123–140.

R. R. Shaffer, U.S. Pat. No. 3,560,616, Feb. 2, 1971, Col. 3, line 48 through Col. 7, line 26 and Exs. 3–9, 11–18.

E. Somers, "Formulation," Chapter 6 in Torgeson, "Fungicides," Vol. I, Academic Press, New York, 1967.

EXAMPLE 4

| Wettable Powder | |
|---|---|
| Dimethyl N,N'-[[1,2-ethanediylbis[thio(methylimino)-carbonyloxy]]]bis(ethanimidothioate) | 40.0% |
| dioctyl sodium sulfosuccinate | 1.5% |
| sodium ligninsulfonate | 3.0% |
| low viscosity methyl cellulose | 1.5% |
| attapulgite | 54.0% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 5

| Wettable Powder | |
|---|---|
| Dimethyl N,N'-[[1,2-ethanediylbis[thio(methylimino)-carbonyloxy]]]bis(ethanimidothioate) | 50.0% |
| sodium alkylnapthalenesulfonate | 2.0% |
| low viscosity methyl cellulose | 2.0% |
| diatomaceous earth | 46.0% |

The ingredients are blended, coarsely hammer milled and then air milled to produce particles of active ingredient essentially all below 10 microns in diameter. The product is reblended before packaging.

EXAMPLE 6

| Wettable Powder | |
|---|---|
| Dimethyl N,N'-[[1,2-ethanediylbis[thio(methylimino)-carbonyloxy]]]bis(ethanimidothioate) | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 7

| Aqueous Suspension | |
|---|---|
| Dimethyl N,N'-[[1,2-ethanediylbis[thio(methylimino)-carbonyloxy]]]bis(ethanimidothioate) | 25.0% |
| hydrated attapulgite | 3.0% |
| crude calcium ligninsulfonate | 10.0% |
| sodium dihydrogen phosphate | 0.5% |
| water | 61.5% |

The ingredients are ground together in a ball or roller mill until the solid particles have been reduced to diameters under 10 microns.

EXAMPLE 8

| Oil Suspension | |
|---|---|
| Dimethyl N,N'-[[1,2-ethanediylbis[thio(methylimino)-carbonyloxy]]]bis(ethanimidothioate) | 25.0% |
| polyoxyethylene sorbitol hexaoleate | 5.0% |
| highly aliphatic hydrocarbon oil | 70.0% |

The ingredients are ground together in a sand mill until the solid particles have been reduced to under about 5 microns. The resulting thick suspension may be applied directly, but preferably after being extended with oils or emulsified in water.

Example 9

| Granule | |
|---|---|
| wettable powder of Example 4 | 10.0% |
| attapulgite granules (U.S.S. No. 20–40; 0.84–0.42 mm) | 90.0% |

A slurry of wettable powder containing 50% solids is sprayed on the surface of attapulgite granules in a double-cone blender. The granules are dried and packaged.

EXAMPLE 10

| Extruded Pellet | |
|---|---|
| Dimethyl N,N'-[[1,2-ethanediylbis[thio(methylimino)-carbonyloxy]]]bis(ethanimidothioate) | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

The ingredients are blended, hammer-milled and then moistened with about 12% water. The mixture is extruded as cylinders about 5 mm diameter which are cut to produce pellets about 3 mm long. These may be crushed to pass a U.S.S. No. 20 sieve (0.84 mm opening). The granules held on a U.S.S. No. 40 sieve (0.42 mm opening) may be packaged for use and the fines recycled.

EXAMPLE 11

| High Strength Concentrate | |
|---|---|
| Dimethyl N,N'-[[1,2-ethanediylbis[thio(methylimino)carbonyloxy]]]bis(ethanimidothioate) | 98.5% |
| silica aerogel | 0.5% |
| synthetic amorphous fine silica | 1.0% |

The ingredients are blended and ground in a hammer mill to produce a high-strength concentrate essentially all passing a U.S.S. No. 50 sieve (0.3 mm opening). This material may then be formulated in a variety of ways.

EXAMPLE 12

| Dust | |
|---|---|
| high-strength concentrate, Example 11 | 25.4% |
| prophyllite, powdered | 74.6% |

The ingredients are thoroughly blended and packaged for use.

EXAMPLE 13

| Emulsifiable Concentrate | |
|---|---|
| Dimethyl N,N'-[[1,2-ethanediylbis[thio(methylimino)carbonyloxy]]]bis(ethanimidothioate) | 20.0% |
| chlorobenzene | 74.0% |
| sorbitan monostearate and polyoxyethylene condensate thereof | 6.0% |

The ingredients are combined and stirred to produce a solution which can be emulsified in water for application.

EXAMPLE 14

| Emulsifiable Concentrate | |
|---|---|
| Dimethyl N,N'-[[1,2-ethanediylbis[thio(methylimino)carbonyloxy]]]bis(ethanimidothioate) | 10.0% |
| blend of oil-soluble sulfonates and polyoxyethylene ethers | 10.0% |
| xylenes | 80.0% |

The ingredients are combined and stirred with gentle warming to speed solution. A fine screen filter is included in packaging operation to insure the absence of any extraneous undissolved material in the product.

Use

The compounds of this invention are useful for control of insects which are detrimental to agriculture.

As demonstrated in Examples 16 to 18 below, improved residual insecticidal properties as well as decreased phytotoxicity are obtained with a formulation containing a compound of Formula I.

The compounds readily control pestiferous insects belonging to such orders as Lepidoptera, Coleoptera, and Diptera. More specifically, insects controlled by the compounds of this invention include but are not limited to: cotton bollworm (*Heliothis zea*), tobacco budworm (*Heliothis virescens*), southern armyworm (*Spodoptera eridania*), beet armyworm (*Spodoptera exigua*), soybean looper (*Pseudoplusia includens*), Mexican bean beetle (*Epilachna varivestis*), and the house fly (*Musca domestica*).

The insects are controlled by applying the compound to the locus of infestation, to the area to be protected, or to the pests themselves. For the control of insects in agricultural crops, a compound of Formula I is generally applied to the foliage or other plant parts which are infested or which are to be protected. Effective amounts to be applied depend upon the species to be controlled, its life stage, its size and location, the amount of rainfall, the time of year, moisture, temperature, type of application, and other variables. In general, 0.1 to 10 kg/ha may be required for insect control in agriculture with rates of 0.2 to 4 kg/ha usually being sufficient in many situations. In large-scale field operations, rates in the range of ¼ to 2 kg/ha are generally used.

The compounds of this invention will generally be used in formulation with a carrier that commonly will contain oil or water. Applications may be made with concentrated or dilute suspensions of the insecticide in the carrier. Low-volume applications utilizing dispersions containing about 20% of the active ingredient may be preferred by some applicators while others may prefer dilute suspensions containing only 25 ppm in high-volume applications.

The compounds of this invention possess significant advantages over prior art compounds, e.g. fewer applications are required to provide a given level of insect control due to this distinctly longer residual insecticidal action. Use of fewer applications results in greater economy to the grower and dissemination of less insecticide in the environment. An additional advantage is lower phytotoxicity to cotton.

Conventionally, the compounds will be incorporated into a formulation in a known manner with incorporation of other components such as (a) surfactants, (b) diluents, (c) additives to reduce foam or corrosion, or (d) preservatives to control microbiological growth.

The compounds of this invention can be mixed with fungicides, bactericides, acaricides, nematicides, other insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides methyl 2-benzimidazolecarbamate;
tetramethyl thiuram disulfide (thiuram);
n-dodecylguanidine acetate (dodine);
manganese ethylenebisdithiocarbamate (maneb);
1,4-dichloro-2,5-dimethoxybenzene (chloroneb);
methyl 1-(butylcarbamoyl)-2-benzimidazolecarbamate (benomyl);
N-trichloromethylthiotetrahydrophthalimide (captan);
N-trichloromethylthiophthalimide (folpet);

Bactericides tribasic copper sulfate;
streptomycin sulfate;

Acaricides senecioic acid, ester with 2-sec-butyl-4,6-dinitrophenol (Morocide ®);
6-methyl-1,3-dithiolo[4,5-b]quinoxalin-2-one (Morestan ®);
ethyl 4,4'-dichlorobenzilate (Folbex ®);
1,1-bis(p-chlorophenyl)-2,2,2-trichloroethane (Kelthane ®);
bis(pentachloro-2,4-cyclopentadien-1yl) (Pentac ®);
tricyclohexyl tinhydroxide (cyhexatin);

Nematicides

S-methyl 1-(dimethylcarbamoyl)-N-(methylcarbamoyloxy)thioformimidate (oxamyl);
S-methyl 1-carbamoyl-N-(methylcarbamoyloxy)thioformimidate;
N-isopropylphosphoramidic acid, O-ethyl-O'-[methylthio)-m-tolyl]diester (fenamiphos);

Insecticides methylcarbamic acid, ester with 2,3-dihydro-2,2-dimethyl-7-benzofuranol (Furadan ®);
0-[2,4,5-trichloro-α-(chloromethyl)benzyl]phosphoric acid, O',O'-dimethyl ester (tetrachlorvinphos); 0-ethyl-0-(4-nitrophenyl)phenylphosphonothioate (EPN);
octachlorocamphene (toxaphene);
cyano(3-phenoxyphenyl)methyl-4-chloro-alpha-(1-methylethyl)benzeneacetate (Pydrin$^{TM}$);
(3-phenoxyphenyl)methyl(±)-cis,trans-3-(2,2-dichloroethenyl)-2,2-dimethylcyclopropanecarboxylate (Ambush ®);
3-phenoxybenzyl-dl-cis,trans-chrysanthemate (phenothrin);
2-mercaptosuccinic acid, diethyl ester, S-ester with thionophosphoric acid, dimethyl ester (malathion);
phosphorothioic acid, O,O-dimethyl, O-p-nitrophenyl ester (methyl parathion);
methylcarbamic acid, ester with α-naphthol (carbaryl);
methyl N-(methylaminocarbonyloxy)ethaneimidothioate (methomyl);
N'-(4-chloro-o-tolyl)-N,N-dimethylformamidine (chlordimeform);
O,O-diethyl-O-(2-isopropyl-4-methyl-6-pyrimidyl-phosphorothioate (Diazinon ®);
O,S-dimethylacetylphosphoramidothioate (acephate);
O,S-dimethylphosphoramidothioate (methamidophos).

EXAMPLE 15

The foliage only of red kidney bean plants in the two-leaf stage was sprayed to run-off with aqueous dispersions of dimethyl N,N'-[[1,2-ethanediylbis[thio(-methylimino)carbonyloxy]]]bis(ethanimidothioate) (I) at the dilutions indicated. The sprays contained Duponol L-144-WDG (sulfonated oleyl acetate surfactant) at a concentration of 1:3000. After drying, a single leaf from each treated plant was excised and placed in a covered 20×100 mm Petri dish containing a moistened filter paper and 10 southern armyworm (SAW) larvae approximately 13 mm in length. The test was conducted in duplicate. Insect mortality was evaluated two days later and is recorded below.

| Treatment | Concentration (% AI) | % Mortality SAW 2 Days |
|---|---|---|
| I | 0.01 | 100 |
|  | 0.005 | 100 |
|  | 0.0025 | 75 |
| untreated control | — | 0 |

EXAMPLE 16

The plants from the test described in Example 1 were kept in a growth room at 77±2° F. and 53±5% relative humidity for 7 days. At the end of that period of time the remaining cotyledonary leaf from each bean plant was placed singly in a Petri dish with southern armyworms as previously described. Insect mortality was again read 2 days later and is set forth below.

| Treatment | Concentration (% AI) | % Mortality SAW 2 Days |
|---|---|---|
| I | 0.01 | 100 |
|  | 0.005 | 95 |
|  | 0.0025 | 50 |
| untreated control | — | 0 |

EXAMPLE 17

Cotton plants approximately 22 cm in height having 3-4 true leaves were sprayed to run-off with an aqueous dispersion of dimethyl N,N'-[[1,2-ethanediylbis[thio(-methylimino)carbonyloxy]]]bis(ethanimidothioate) (I) at a concentration of 0.05%. The spray contained Duponol L-144-WDG at a concentration of 1:3000. Another set of plants was similarly treated with methomyl. Plant injury was evaluated 6 days after treatment and is recorded below.

| Treatment | Injury Rating* |
|---|---|
| I | slight trace |
| methomyl | 3 |

*Scale:
0 = no injury
10 = plant killed

What is claimed is:
1. A compound of the formula

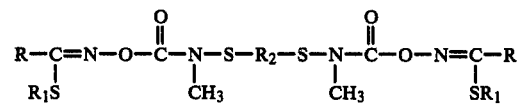

wherein
R is branched or straight chain alkyl containing 1 to 3 carbon atoms or methoxymethyl;
$R_1$ is branched or straight chain alkyl containing 1 to 3 carbon atoms;
$R_2$ is —CH$_2$CH$_2$—,

or —CH$_2$CH$_2$ZCH$_2$CH$_2$—; and
Z is O or S.

2. The compound of claim 1 wherein R is methyl or ethyl and R$_1$ is methyl.

3. The compound of claim 2 wherein R is methyl and R$_2$ is —CH$_2$CH$_2$—.

4. The compound of claim 3 which is dimethyl —N,N'-[[1,2-ethanediylbis[thio(methylimino)carbonyloxy]]]bis(ethanimidothioate) having the formula:

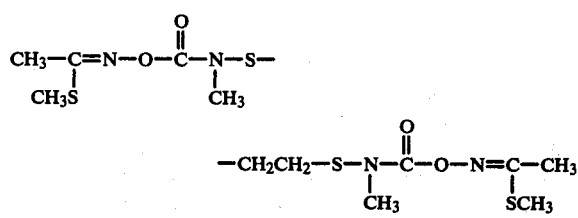

5. A composition suitable for control of pestiferous insects consisting essentially of an insecticidally effective amount of a compound of claim 1 and at least one of (a) an inert diluent and (b) a surfactant.

6. A composition suitable for control of pestiferous insects consisting essentially of an insecticidally effective amount of a compound of claim 2 and at least one of (a) an inert diluent and (b) a surfactant.

7. A composition suitable for control of pestiferous insects consisting essentially of an insecticidally effective amount of a compound of claim 3 and at least one of (a) an inert diluent and (b) a surfactant.

8. A composition suitable for control of pestiferous insects consisting essentially of an insecticidally effective amount of the compound of claim 4 and at least one of (a) an inert diluent and (b) a surfactant.

9. A method for control of pestiferous insects which comprises applying to a locus of infestation, to the area to be protected or to the pests themselves, an insecticidally effective amount of a compound of claim 1.

10. A method for control of pestiferous insects which comprises applying to a locus of infestation, to the area to be protected or to the pests themselves, an insecticidally effective amount of a compound of claim 2.

11. A method for control of pestiferous insects which comprises applying to a locus of infestation, to the area to be protected or to the pests themselves, an insecticidally effective amount of a compound of claim 3.

12. A method for control of pestiferous insects which comprises applying to a locus of infestation, to the area to be protected or to the pests themselves, an insecticidally effective amount of the compound of claim 4.

* * * * *